US011044935B2

(12) United States Patent
Puupponen-Pimiä et al.

(10) Patent No.: US 11,044,935 B2
(45) Date of Patent: Jun. 29, 2021

(54) PROCESS FOR CONVERTING BERRY AND FRUIT MATERIALS TO ANTIMICROBIALLY ACTIVE FRACTIONS

(71) Applicant: TEKNOLOGIAN TUTKIMUSKESKUS VTT OY, Espoo (FI)

(72) Inventors: Riitta Puupponen-Pimiä, Vtt (FI); Liisa Nohynek, Vtt (FI); Tuija Kössö, Vtt (FI); Mirja Mokkila, Vtt (FI)

(73) Assignee: TEKNOLOGIAN TUTKIMUSKESKUS VTT OY, Espoo (FI)

( * ) Notice: Subject to any disclaimer, the term of this patent is extended or adjusted under 35 U.S.C. 154(b) by 751 days.

(21) Appl. No.: 15/537,349

(22) PCT Filed: Dec. 17, 2015

(86) PCT No.: PCT/FI2015/050896
§ 371 (c)(1),
(2) Date: Jun. 16, 2017

(87) PCT Pub. No.: WO2016/097488
PCT Pub. Date: Jun. 23, 2016

(65) Prior Publication Data
US 2018/0263272 A1    Sep. 20, 2018

(30) Foreign Application Priority Data
Dec. 19, 2014    (FI) .................................... 20146128

(51) Int. Cl.
| *A23N 7/01* | (2006.01) |
| *A61K 36/87* | (2006.01) |
| *A61K 8/9789* | (2017.01) |
| *A61K 36/73* | (2006.01) |
| *C12P 19/02* | (2006.01) |
| *C12P 17/06* | (2006.01) |
| *C12P 19/14* | (2006.01) |
| *A61Q 19/00* | (2006.01) |
| *A61Q 17/00* | (2006.01) |
| *A23L 5/30* | (2016.01) |
| *A23N 7/08* | (2006.01) |
| *A61K 36/738* | (2006.01) |

(52) U.S. Cl.
CPC ................. *A23N 7/01* (2013.01); *A23L 5/30* (2016.08); *A23N 7/08* (2013.01); *A61K 8/9789* (2017.08); *A61K 36/73* (2013.01); *A61K 36/738* (2013.01); *A61K 36/87* (2013.01); *A61Q 17/005* (2013.01); *A61Q 19/00* (2013.01); *C12P 17/06* (2013.01); *C12P 19/02* (2013.01); *C12P 19/14* (2013.01); *A23Y 2220/00* (2013.01); *A23Y 2280/00* (2013.01); *A61K 2236/00* (2013.01); *A61K 2236/13* (2013.01); *A61K 2236/15* (2013.01); *A61K 2236/19* (2013.01); *A61K 2236/37* (2013.01); *A61K 2800/10* (2013.01); *A61K 2800/74* (2013.01)

(58) Field of Classification Search
CPC ........ A61K 36/29; A61K 36/60; A61K 36/87; A61K 36/45; A61K 2300/00; A61K 36/73; A61K 2236/00; A61K 2236/13; A61K 2236/15; A61K 2236/19; A61K 2236/37; A61K 2800/10; A61K 2800/74; A61K 36/738; A61K 8/9789; A23L 5/30; A23N 7/01; A23N 7/08; A23Y 2220/00; A23Y 2280/00; A61Q 17/005; A61Q 19/00; C12P 17/06; C12P 19/02; C12P 19/14; A61P 31/04
USPC ................................ 424/732, 766, 776, 777
See application file for complete search history.

(56) References Cited

U.S. PATENT DOCUMENTS 5,580,787 A * 12/1996 Wessels ............... C07K 14/335
                                                       424/93.45
2010/0280132 A1    11/2010 Berggren et al.
2013/0040005 A1    2/2013 Hirayama et al.

FOREIGN PATENT DOCUMENTS

| CN | 1233427 A | 11/1999 |
| CN | 1823856 A | 8/2006 |
| CN | 101077163 A | 11/2007 |
| CN | 101715347 A | 5/2010 |
| CN | 102613639 A | 8/2012 |
| CN | 203290214 U | 11/2013 |
| CN | 104120056 A | 10/2014 |
| FI | 122664 B | 5/2012 |

(Continued)

OTHER PUBLICATIONS

Xu et al. "Extraction, distribution and characterisation of phenolic compounds and oil in grapeseeds", Food Chemistry 122 (2010) 688-694). (Year: 2010).*
Vincent Gallon "Polyphenols extracted from berry seeds can have a selected antimicrobial effect, finds Finnish research centre" Premium Beauty News, retreived online from URL: premiumbeautynews.com/en/polyphenols-extracted-from-berry,12054>, Sep. 4, 2017, 3 pages. (Year: 2017).*
Finnish Search Report, issued in Finnish Priority Application No. 20146128, dated Aug. 19, 2015.
Abstract of HU 0600829 A2 dated Nov. 28, 2008.

(Continued)

*Primary Examiner* — Aaron J Kosar
(74) *Attorney, Agent, or Firm* — Birch, Stewart, Kolasch & Birch, LLP

(57) ABSTRACT

The invention relates to process for converting berry and/or fruit materials to fractions comprising bioactive compounds, said process comprising the steps, where at least one berry material or fruit material selected from berries, fruits, by-products, side streams and waste materials originating from berries or fruits, and any combinations thereof is sieved whereby a seed fraction is separated from a skin fraction, the seed fraction is subjected to sanding and a seed coat fraction comprising surface layer of the seeds and a sanded seed fraction comprising the sanded seeds are obtained.

14 Claims, 3 Drawing Sheets

(56) References Cited

FOREIGN PATENT DOCUMENTS

| | | |
|---|---|---|
| JP | 2006-503059 A | 1/2006 |
| JP | 2012-115234 A | 6/2012 |
| RU | 2 412 717 C1 | 2/2011 |
| WO | WO 2004/026325 A2 | 4/2004 |
| WO | WO 2004/087185 A1 | 10/2004 |
| WO | WO 2005/072762 A1 | 8/2005 |
| WO | WO 2007/026101 A1 | 3/2007 |
| WO | WO 2011/015706 A1 | 2/2011 |

OTHER PUBLICATIONS

International Search Report, issued in PCT/FI2015/050896, dated Mar. 24, 2016.

Puupponen-Pimiä et al., "Antimicrobial properties of phenolic compounds from berries," Journal of Applied Microbiology (2001), vol. 90, pp. 494-507.

Puupponen-Pimiä et al., "Bioactive berry compounds—novel tools against human pathogens," Appl. Micorbiol. and Biotechnol. (2005), vol. 67, pp. 8-18.

Puupponen-Pimiä et al., "Fermentation and dry fractionation increase bioactivity of cloudberry (*Rubus chamaemorus*)," Food Chemistry (Apr. 2016) vol. 197, pp. 950-958.

Written Opinion of the International Searching Authority, issued in PCT/FI2015/050896, dated Mar. 24, 2016.

Xu et al., "Extraction, distribution and characterisation of phenolic compounds and oil in grapeseeds," Food Chemistry (2010), vol. 122, pp. 688-694.

Chingwaru et al., "Antibacterial and anticandidal activity of *Tylosema esculentum* (marama) extracts," S. Afr. J. Sci. (2011), vol. 107, No. 3/4, pp. 1-11.

Extended European Search Report dated Jul. 26, 2018, in European Patent Application No. 15869407.5.

Nohynek et al., "Berry Phenolics: Antimicrobial Properties and Mechanisms of Action Against Severe Human Pathogens," Nutrition and Cancer (2006), vol. 54, No. 1, pp. 18-32.

Office Action dated May 16, 2019, in Russian Patent Application No. 2017125513/13(044038), with English translation.

English translation of Japanese Office Action for Japanese Application No. 2017-551366, dated Jul. 23, 2019.

Partial English translation of Kouso riyou hand bukku, Tijin shokan, 1988 nen 9 gatsu 20 nichi, Shohan Dai 4 satsu, pp. 323-324 (4 pages total).

Partial English translation of Shokuhin kougyou riyou biseibutsu de-ta bukku, Tokyo kagaku doujin, 1994 nen, Dai 1 pan Dai 1 satsu, 76-77.

Chinese Office Action and Search Report, dated Dec. 26, 2019, for Chinese Application No. 201580076575.4, with English translations.

Baydar et al., "Total phenolic contents and antibacterial activities of grape (*Vitis vinifera* L.) extracts," Elsevier, Food Control, vol. 15, 2004, pp. 335-339.

Japanese Office Action for Japanese Application No. 2017-551366, dated Jul. 23, 2019.

Kouso riyou hand bukku, Tijin shokan, 1988 nen 9 gatsu 20 nichi, Shohan Dai 4 satsu, pp. 323-324 (4 pages total).

Phillips, "Preparation and Composition of a Dry-Milled Flour from Cowpeas," J Am Oil Chemists' Soc., vol. 59, No. 8, Aug. 1982, pp. 351-353.

Shokuhin kougyou riyou biseibutsu de-ta bukku, Tokyo kagaku doujin, 1994 nen, Dai 1 pan Dai 1 satsu, 76-77.

Wang, "Optimization of a Laboratory Dehulling Process for Lentil (*Lens culinaris*)," Cereal Chem., vol. 82, No. 6, 2005, pp. 671-676 (9 pages total).

Chinese Office Action and Search Report, dated Aug. 4, 2020, for Chinese Application No. 201580076575.4, with English translations.

\* cited by examiner

PROCESS FOR CONVERTING BERRY AND FRUIT MATERIALS TO ANTIMICROBIALLY ACTIVE FRACTIONS

FIELD OF THE INVENTION

The present invention relates to a process for converting berry and fruit materials to fractions comprising bioactive compounds with antimicrobial activity. The invention also relates to fractions comprising bioactive compounds with antimicrobial activity, originating from berries and fruit, obtainable by the process. The invention further relates to the use of said fractions comprising bioactive compounds with antimicrobial activity in cosmetics, hygiene products, nutraceuticals, food products and food supplements, feeds, packages and in pharmaceutical products.

BACKGROUND OF THE INVENTION

In the industry dealing with processing of berries and fruits significant amounts of waste materials, side streams and by-products are formed. Food industry uses wild berries, cultured berries and fruits in the manufacture of wide range of products, such as pastes, beverages, alcohol products, jams, conserves, milk based products, sweets and the like. The use of berry and fruit fractions has also become very popular in cosmetic products and for example cloudberry seed oil, rich in polyunsaturated fatty acids, is regarded as a valuable component in cosmetic preparations.

Large volumes of waste are produced in the processing of berries and fruit, particularly in the food industry, which waste material is utilized to a very small extent. Most of the waste material is currently discarded or transported to landfill or dumping area, thus increasing the environmental burden. Some of this waste material is subjected to drying followed by extraction of seed oils, however only a very small portion of the material is used.

Typically, in the processing, berries and fruit are mechanically cleaned, followed by removing of the juice, pulp or paste by suitable methods, such as pressing. The remaining waste material, such as pomace, berry cake, fruit cake or press cake comprises berry or fruit skins, peels, seeds and pith, which contain bioactive phenolic compounds, fibers and other bioactive compounds.

FI 122664 B discloses a method for fractionating berries and separating nutrients from the fractions formed, in which method berry raw material is dried and ground lightly, so that the seeds of the berry separate from the fruit flesh and skin portion without breaking, followed by a second light grinding, which is carried out on the formed seedless fruit flesh and skin fraction, whereby a fine powder is formed, which is screened or classified. Seeds are not fractionated by this method. Seed are discarded and peels are further fractionated.

US 2013/0040005 A1 relates to an antihypertensive agent comprising boysenberry seed extract as active ingredient and to a method for obtaining said agent. In said method boysenberry pomace is dried, crushed and sieved to separate the seed, followed by grinding the seed to fine powder, which is extracted with water or organic solvent, followed by contacting the extraction solution with a polyphenol absorbent and eluting with alcohol based solvent to obtain the target extract.

Based on the above it can be seen that there still exists a need to provide improved methods for utilizing berry and fruit materials, particularly waste materials, side streams and by-products for providing fractions comprising valuable bioactive compounds contained in said materials.

SUMMARY

In the present invention it was found that fractions comprising bioactive compounds, with strong antimicrobial activity, originating from berry and/or fruit seeds, can be enriched with a simple method.

The present invention is particularly based on studies on processing of pomace, berry cake, fruit cake and press cake obtained from berries and fruit, and the use of the obtained products. The invention provides convenient and effective means particularly for utilizing waste materials, side streams and by-products from berry and fruit industry, such as pomace, press cake, berry cake and fruit cake, in the manufacture of fractions comprising bioactive compounds useful in cosmetics, hygiene products, food supplements, food products, feeds, packages and in pharmaceutical products, particularly as natural antimicrobials or natural preservatives.

Thus an object of the invention is to provide a process for converting berry materials and/or fruit materials to fractions comprising bioactive compounds with antimicrobial activity.

A further object of the invention is to utilize waste materials, side streams and by-products from berry industry and/or fruit industry without the need to discard said materials.

A further object of the invention is to provide fractions comprising bioactive components originating from berries and fruits.

A still further object of the invention is the use of said fractions comprising bioactive compounds in cosmetics, hygiene products, nutraceuticals, food products, food supplements, feeds, packages and in pharmaceutical products.

The invention is directed a process for converting berry and/or fruit materials to fractions comprising bioactive compounds with antimicrobial activity, which process comprises the steps, where at least one berry material or fruit material selected from berries, fruits, by-products, side streams and waste materials originating from berries or fruits, and any combinations thereof, having water content not more than 15 wt %, is sieved, whereby a seed fraction is separated from a skin fraction, the seed fraction is subjected to sanding where 2-40 wt % of the seed is removed and a seed coat fraction comprising surface layer of the seeds and a sanded seed fraction comprising the sanded seeds are obtained, and the berries are selected from the genus *Rubus, Sorbus, Rosa, Empetrum, Aronia* and *Hippophae* and from combinations thereof, and the fruit are selected from the genus *Vitis, Punica, Pyrus* and *Malus*, and combinations thereof.

The invention is further directed to the use of the seed coat fraction comprising antimicrobially active compounds, in cosmetics, hygiene products, nutraceuticals, food products, food supplements, feeds, packages and in pharmaceutical products.

Accordingly, the present invention provides simple and economic means for utilizing waste materials, side streams and by-products originating from berry industry and fruit industry in the manufacture of fractions comprising bioactive compounds, whereby dumping of berry or fruit waste can be avoided or at least substantially decreased.

DEFINITIONS

Figure 1:
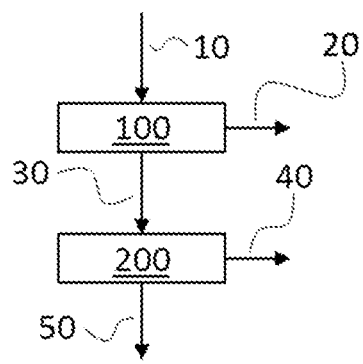
FIG. 1 illustrates one embodiment of the process of the invention.

Unless otherwise specified, the terms, which are used in the specification and claims, have the meanings commonly used in the field of food industry. Specifically, the following terms have the meanings indicated below.

The term "berry" is understood here to mean all wild and cultivated berries comprising internal seeds, which berries belong to the genus *Rubus, Sorbus, Empetrum, Rosa, Aronia* or *Hippophae*, including all hybrid berries of these genera. Raspberries, blackberries, arctic bramble, dewberries and cloud berries are examples of the *Rubus* species. As the *Rubus* species readily interbreed and are apomicts, the parentage of the hybrid plants is often highly complex, but it is generally agreed to include in the definition cultivars of blackberries and raspberries. Examples of said hybrid berries include loganberry, boysenberry, veitchberry, marionberry, silvanberry, tayberry, tummelberry and hildaberry.

The term "fruit" is understood here to mean all wild and cultivated fruit belonging to the genus *Vitis, Punica, Pyrus* and *Malus*, including all hybrid fruit of these genera.

Fruit of the genus *Vitis* mean grapes comprising internal seeds, including all hybrid grapes, which are primarily crosses between *V. vinifera* and another grapevine. Grapes are used for making wine, jam, beverages, jelly, seed extract, raisins, vinegar, and grape seed oil. *Vitis* is a genus of about 60 vining plants in the family Vitaceae.

Fruits refers also to fruits of fruit trees, such as pomegranate (*Punica granatum*), pear tree (*Pyrus communis*) and apple tree (*Malus* family) and all hybrids thereof.

The terms "berry industry" and "fruit industry" refer to industry dealing with the development, refining and manufacture of products and processes relating to wild and cultivated berries and fruit.

The term "antimicrobially active" compound refers here to compounds being able to kill microorganisms or inhibit their growth. Examples of these compounds are phenolic compounds, such as ellagic acid and ellagitannins. In addition to antimicrobial and preservative activity, these compounds often have other biological activities, particularly antioxidant activity.

The term "sanding of seeds" refers here to mechanical, abrasive treatment where the surface layer of the seeds is removed as powder. Sanding is understood to also include polishing and pearling.

The term "cosmetics" refers here to cosmetic products including skin care products, hair care products, personal care products, colour cosmetics. Examples of skin care products are oily creams, basic creams, toners, exfoliators, wipes, masks and the like.

DETAILED DESCRIPTION OF THE INVENTION

The invention provides a convenient process for converting berry materials and fruit materials to fractions comprising valuable bioactive compounds, particularly to fractions comprising significant amounts of phenolic compounds, such as ellagic acid and ellagitannins. Ellagitannins are esters of glucose with ellagic acid which, when hydrolysed, yield ellagic acid.

The invention is based on studies on the processing of waste materials, side streams and by-products originating from processing of berries and fruit, such as pomace and press cake, for providing means for utilizing these waste materials and by-products in the manufacture of fractions comprising bioactive compounds, useful for example in cosmetics, hygiene products, nutraceuticals, food products, food supplements, feeds, packages and in pharmaceutical products, as natural preservatives.

It was found that particularly the surface layer (seed coat fraction) of the seeds of berries of the genus *Rubus, Sorbus, Empetrum, Rosa, Aronia* and *Hippophae* and seeds of the fruits of the genus *Vitis, Punica, Pyrus* and *Malus* shows strong antimicrobial activity for example against the human pathogen *Staphylococcus aureus*. The seed coat fractions contain high concentrations of bioactive phenolic compounds. Particularly ellagic acid, ellagitannins and derivatives thereof are comprised in said fractions of *Rubus* berries.

Remarkable amounts of biologically active phenolic compounds, such as ellagic acid and ellagitannins and their derivatives remain in the waste material which is currently not utilized. Ellagic acid and ellagitannins are natural antioxidants and preservatives having strong antimicrobial effect, thus useful as natural preservatives and antioxidants in various applications in the field of cosmetics, food industry and feed industry, as well as in packaging industry and pharmaceutical industry.

With the process of the invention berry skins or fruit skins can be separated from the seeds and the seed surface layer can then be removed to obtain seed coat fraction having high antimicrobial activity. Further, the sanded seeds may be used as such or treated enzymatically, and the berry skin or fruit skin fraction finds its uses too.

Berries

In the present invention, all wild berries, cultivated berries and all hybrid berries of the genus *Rubus, Sorbus, Empetrum, Rosa, Aronia* and *Hippophae* and any combinations thereof may be used. Raspberries, blackberries, arctic bramble (synonym arctic raspberries), dewberries and cloudberries, and hybrid berries including loganberry and boysenberry are examples of the *Rubus* species suitable for the invention. Rowanberry is an example of *Sorbus* species, crowberry of *Empetrum* species, rose hip and dog rose of Rosa species, chokeberry of *Aronia* species and sea buckthorn berry of *Hippophae* species suitable for the invention.

Cloudberries are valuable wild berries having high aroma content and they contain also valuable seed oil. Cloudberries are used in food, liqueur and cosmetic industry, however only the seed oil is presently utilized from the waste material remaining after pressing the berries. Ellagic acid content found in cloudberry were the following: berry fruit (fruit+seeds) 0.6 mg/g dry weight, skins 20.3 mg/g dry weight, sanded seed coat power 19.6 mg/g dry weight and polished seeds 12.6 mg/g dry weight. Ellagitannins were concentrated in the sanded seed coat fraction.

Arctic brambles contain very high ellagic acid and ellagitannin contents and thus they are also particularly suitable as raw material for the process of the invention. From the ecological point of view, wild berries, such as cloudberries and arctic bramble which have grown without any manmade fertilizers or pesticides, are particularly suitable.

Fruits

All fruits of the genus *Vitis, Punica, Pyrus* and *Malus* are suitable for the process of the invention. All grapes and all hybrid grapes, containing seeds and belonging to the genus *Vitis* may be used in the present invention. Typically huge amounts of waste material are obtained from processing of grapevines, such as from pressing grapevines and thus grapes offer also a particularly suitable raw material source for the present invention.

Fruits of fruit tree, such as pomegranate (*Punica granatum*), pear tree (*Pyrus communis*) and apple tree (*Malus* family), including all hybrids thereof are also suitable raw material source. Remarkable amounts of waste material are obtained during processing of these fruits.

Berry Materials and Fruit Materials

The berry materials and fruit materials suitable for the process of the invention may be selected from whole berries, whole fruits, by-products, side streams and waste materials, originating from processing of berries or fruit. Examples of such by-products, side streams and waste materials are press cakes, pomaces, berry cakes and fruit cakes. Said by-products, side streams and waste material typically comprise berry or fruit skins or peels, seeds, some pulp, occasionally some leaves, arbors and conifer needles, depending also how well the berries or fruit are cleaned mechanically before processing.

Processing of berries or fruit may be carried out for example at a facility carrying out processing or refining or fractionating of berries or fruit, or at a facility in the food or feed processing industry, from the manufacture of beverages, pastes, purees, wines, jams, conserves, sweets and the like. Particularly preferably by-products, side streams and waste materials are used in the present invention.

Typically in a juicing line, berries or fruit are pressed and the remaining press cake is frozen and stored at approx. −20° C. for further use, or alternatively it may be dried.

Berry and fruit pastes and purees are obtained for example by squeezing berries or fruit through a sieve and the remaining berry cake or fruit cake is frozen and stored at approx. −20° C., or alternatively it may be dried. The obtained frozen pomace, berry cake or fruit cake may contain from 40 to 70% by weight of water, typically from 50 to 60% by weight of water.

The by-products, side streams or waste material obtained from the berries of the genus *Rubus* or grapes from the genus *Vitis*, such as press cake or pomace contains predominantly seeds, skins or peels and some pulp.

Process

The present invention is directed a process for converting berry and/or fruit materials to fractions comprising bioactive compounds with antimicrobial activity, which process comprises the steps, where at least one berry material or fruit material selected from berries, fruits, by-products, side streams and waste materials originating from berries or fruits, and any combinations thereof, having water content not more than 15 wt %, is sieved whereby a seed fraction is separated from a skin fraction, the seed fraction is subjected to sanding where 2-40 wt % of the seed is removed and a seed coat fraction comprising surface layer of the seeds and a sanded seed fraction comprising the sanded seeds are obtained, and where the berries are selected from the genus *Rubus, Sorbus, Rosa, Empetrum, Aronia* and *Hippophae* and from combinations thereof, and the fruit are selected from the genus *Vitis, Punica, Pyrus* and *Malus*, and combinations thereof.

The berry material or fruit material having water content not more than 15 wt % means here dry berry material or fruit material.

The process of the invention is illustrated in FIG. 1, where berry and/or fruit material 10 having water content not more than 15 wt %, is subjected to sieving 100, whereby a seed fraction 30 is separated from a skin fraction 20, the seed fraction 30 is subjected to sanding 200 where 2-40 wt % of the seed is removed and a seed coat fraction 50 comprising surface layer of the seeds and a sanded seed fraction 40 comprising the sanded seeds are obtained.

The seed fraction comprises seeds. Occasionally it may comprise small amounts of any of skin, peel and pulp.

The skin fraction comprises skin, peel and pulp. Occasionally it may comprise small amounts of any of leaves, arbors and conifer needles.

In a preferable embodiment the berry and/or fruit material has water content of 0.1-10 wt %, particularly preferably 0.1-8 wt %.

In the process sieving (separation of seeds) is carried out, where the berry material or fruit material having water content not more than 15 wt % is sieved, whereby the seeds remain on the sieve and the skin, peels, pulp etc pass through the sieve.

Suitably a sieving device, air classification device, air jet sieve device, screening device or rotary screen is used, preferably a vibratory or a shaking sieving/screening device is used, where the sieve size is selected according to the seed size of the berry or fruit.

For example, when sieving berry material obtained from the genus *Rubus* suitably a sieve is used where the sieve has a mesh opening of 0.5-2.0 mm, preferably 0.6-1.6 mm.

The sanding is carried out using a sanding or polishing apparatus selected from grain polishing machines (e.g. barley), rice etc. polishing machines, pearling machines, dehullers and polishers/hullers.

In the sanding from 2 to 40 wt %, preferably 3-35 wt %, particularly preferably from 3 to 30 wt % of the seed surface layer is removed as finely divided powder fraction (seed coat fraction) from the seeds and a sanded seed fraction is also obtained.

Pretreatment of Berry Material or Fruit Material

In an embodiment of the invention the berry material or fruit material is pretreated prior to sieving. The pretreatment may be carried by subjecting the berry material or fruit material to methods selected from heat treatment, fermentation, enzymatic treatment, pressing, squeezing, drying, crushing and combinations thereof.

According to one embodiment of the invention the berry material or fruit material is pressed, separated, decanted or centrifuged to separate the juice from solid matter (peels and seeds).

According to one embodiment of the invention the berry material or fruit material is heat treated for the removal of harmful microbes. Suitably the heat treatment is carried out at 80° C. for 5 min.

According to one embodiment of the invention the berry material or fruit material is fermented using lactic acid bacteria to modify the phenolic compounds and the carbohydrate components of the seed. Preferably the starter culture is selected from the genera *Lactococcus, Lactobacillus, Pediococcus* and *Oenococcus*.

Figure 2:
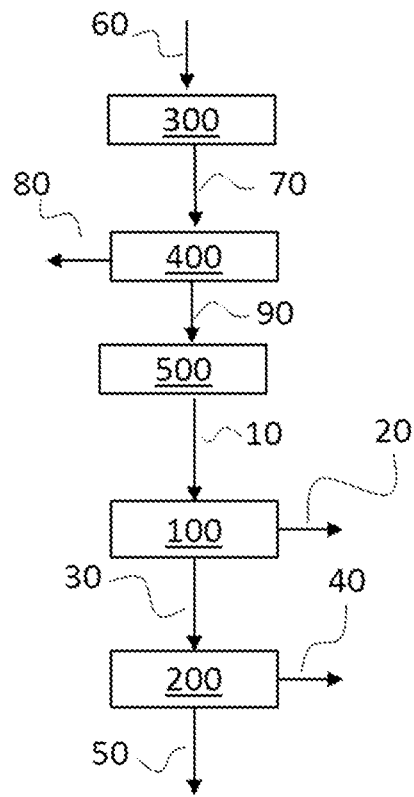
FIG. 2 illustrates another embodiment of the process of the invention, where berry or fruit material is pretreated prior to sieving.

FIG. 2 illustrates an embodiment where the berry material or fruit material is pretreated prior to sieving. Berry material or fruit material 60 is subjected to heat treatment and fermentation 300 whereby fermented berry or fruit material 70 is obtained, which is then subjected to pressing 400, whereby juice fraction 80 is separated from press cake 90. The press cake 90 is subjected to drying 500 to obtain berry material or fruit material 10 having water content not more than 15 wt %, which is subjected to sieving 100, whereby a seed fraction 30 is separated from a skin fraction 20, the seed fraction 30 is subjected to sanding 200 where 2-40 wt % of the seed is removed and a seed coat fraction 50 comprising surface layer of the seeds and a sanded seed fraction 40 comprising the sanded seeds are obtained.

In the fermentation typically frozen berry or fruit material and water, suitably ultra-pure water, are mixed together (1:1) and heated, suitably at 80° C. for 5 min. The mixture is cooled, suitably in an ice bath and if needed berry or fruit material is crushed. The pH of the mixture is adjusted to approx. pH 5.0, suitably with 5 N sodium hydroxide. The microbes are pre-grown in food-grade media. The fermentation is carried out in a bioreactor (a vessel) etc., for example for 3 days at 30° C. under constant mixing. Lactic acid bacteria fermentations are purged with sterile nitrogen gas to create anaerobic conditions.

According to one embodiment of the invention the berry material or fruit material is treated with carbohydrate hydrolyzing enzymes. The berry material or fruit material is preferably pressed or squeezed after the enzyme incubation. Suitably the enzyme is selected from cellulose, pectinase, xylanase and combinations thereof. The juice yield is increased and the press cake or berry cake contains decreased amounts of sugars and water.

In the enzyme treatment the enzymes are dosed based on their main activity (e.g. 100 nkat/g or 0.1%). Thawed, mashed and heated (45° C.) berry or fruit material is incubated at 40-45° C. for 2-4 hours. Enzyme is diluted in water before mixing with the mashed and heated berry and fruit materials. The treatments are carried out at the intrinsic pH of the used material (about pH 3). After enzyme incubations, the berry or fruit juice is extracted by a juice pressing device.

According to one embodiment of the invention the berry material or fruit material is dried prior to introducing to the process for removing excess water, until it has water content of not more than 15 wt %, preferably 0.1-10 wt %. The drying may be carried out as convective drying, such as hot-air drying, vacuum drying or steam drying, microwave drying with or without vacuum drying, or freeze-drying. The drying may be carried out using a fluid-bed drier at a temperature from 35 to 70° C. preferably 35-45° C. Suitably the freeze drying is carried out at a temperature from −40 to 0° C., and convective drying at a temperature from 40 to 70° C., preferably from 40 to 50° C. Any conventional drying devices suitable for the drying can be used.

According to one embodiment the berry material or fruit material is crushed prior to sieving, suitably using compression crushing to break lumps of skin, peels, pulp etc from the seeds and to cause minimum damage to the seeds. The crusher may be selected from roll crusher, a ball crusher, manual type crusher, a kneader grinder or a combination thereof. A kneader grinder may be used as the crusher, by which the seeds of the berry are detached from the dry pulp and skin portion without breaking the seeds. A suitable grinder is a falling number mill containing a rotating rotor and a stationary stator. This mill provides a kneading and slightly cutting and striking effect, wherein the grinding energy is, however, not sufficient to break the seeds, but they are detached from the matrix. A disc mill or an impact mill with a guided impact is preferably used, whereby a gentler grinding process is achieved.

The sanded seeds comprising the seed core and the seed oil may be used as such in food and animal feed applications as healthy nutritional components. Alternatively the sanded seeds may be treated with an enzyme.

The sanded seed fraction may be further treated with an enzyme selected from cellulase, pectinase, xylanase and combinations thereof to soften the still existing seed coat, preferably combinations are used. As the seed coat is thinner and further softer after the enzyme treatment, the healthy fatty acids can be delivered more easily from the seeds during consumption and the mouth-feel is also better as the seed coat is softer. These sanded and enzyme treated seeds are particularly useful in various food applications, for example in snacks, cereals, muesli, bakery products, etc., and is animal feeds.

Figure 3:
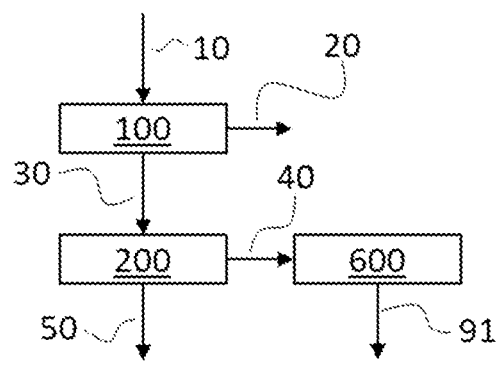
FIG. 3 illustrates still another embodiment of the process of the invention, where the sanded seeds are subjected to enzyme treatment.

FIG. 3 shows an embodiment where the sanded seed fraction is subjected to enzymatic treatment. Berry material and/or fruit material 10 having water content not more than 15 wt % is subjected to sieving 100, whereby a seed fraction 30 is separated from a skin fraction 20, the seed fraction 30 is subjected to sanding 200 where 2-40 wt % of the seed is removed and a seed coat fraction 50 comprising surface layer of the seeds and a sanded seed fraction 40 comprising the sanded seeds are obtained. The sanded seed fraction 40 is subjected to enzyme treatment 600, whereby enzyme treated sanded seed fraction 91 is obtained. Before the enzyme treatment the seeds are suitably soaked in water overnight (not shown in the figure).

The enzyme treated sanded seeds may also be subjected to extraction of phenolics or seed oil using suitable extraction technique, such as conventional super critical or solvent extraction methods or combinations thereof. The enzyme treatment improves the extraction of fatty acids from the sanded seeds, whereby valuable seed oil may be obtained.

Alternatively the sanded seeds may be milled, followed by optional dry fractionation.

The fiber rich berry skin or fruit skin fraction separated from the seeds may be used as such or it may be further ground finer by a suitable mill, which is preferably a pin crusher. The amount of the skin fraction is typically 2-10 wt % of the berry material or fruit material, calculated on dry basis. As an example the skin fraction of cloudberry contains typically ellagic acid 20 mg/g dry weight. It may be used as an ingredient in cosmetics, food products and animal feeds.

The obtained seed coat fractions are rich in phenolic compounds, such as ellagic acid, ellagitannins and their derivatives and other bioactive compounds. Said seed coat fractions can be used as natural preservatives in cosmetics, hygiene products, nutraceuticals, food products, food supplements, animal feeds, packages and in pharmaceutical products.

The seed coat fractions comprising the bioactive components are suitably incorporated in food products, in cosmetic products, in pharmaceutical products, in animal feeds, in packaging materials, particularly in packaging materials of products, such as food which is easily spoiled, and in pharmaceuticals, such as topical products like creams, ointments, etc.

Examples of said easily spoiled food products are poultry products, such as marinades, milk based products, such as yoghurts, drinks, sour cream products, fermented milk based products; berry or fruit containing products, such as jams, beverages, berry soups, conserves, pastes, purees, baby food; nutritional food products, particularly for special use, such as hospital use and hose administration; grain products, such as bread, cereals, snack products, muesli, precooked porridge, fermented grain based products and gluten-free products.

The present invention provides several advantages. Particularly the by-products, side streams and waste materials originating from berry and fruit processing industry can be effectively utilized in the simple and economic process of the invention, for obtaining fractions comprising valuable bioactive components, as well as skin fractions and sanded seed fractions, which also find several valuable uses. With the process of the invention practically all the waste and by-product material can be utilized effectively.

Said bioactive fractions may be used as effective antioxidants, antimicrobial agents and preservatives, particularly in the field of cosmetics, food products and animal feeds, as well as in packages and in pharmaceutical products.

The process of the invention provides enrichment of phenolic compounds, such as of ellagic acid and ellagitannin and their derivatives, whereby said compounds are concentrated in specific fractions for further use. The specific fractions can be added as such to various products. Dumping of the waste materials to the landfills can be avoided or at least significantly reduced. This is also a clear environmental and ecological benefit. Nutritionally rich and valuable waste materials and by-products from the berry industry and fruit industry can be utilized in a simple and efficient way in food products and animal feeds, as well as in packages and in pharmaceutical products.

The invention provides improved storage and microbiological safety to the products, as these fractions comprising the bioactive compounds act as preservatives. It is possible to decrease the amount of synthetic preservatives in the products and replace them by these natural compounds. In addition, in cosmetic products these natural compounds also balance skin microbiota, as they effectively inhibit the growth of skin pathogens, such as *Staphylococcus*.

The invention provides improved microbiological preservation, improved inhibition of oxidation reactions and increased antioxidant status to the products. In general this means improved stability and microbiological safety.

EXAMPLES

The following examples are illustrative of embodiments of the present invention, as described above, and they are not meant to limit the invention in any way.

Example 1: Sanding of Cloudberry Seeds Separated from Press Cake

A dried pressed cake of cloudberry from a commercial juice pressing process was sieved. The seeds were separated from the skin fraction by using a vibratory sieve shaker with a 1.6 mm screen at settings of 10 minutes sieving time and 1.5 mm amplitude. The seeds were sanded by using an abrasive machine (barley pearling machine) for 15 minutes sanding time. Table 1 shows yields obtained by the different process steps and distribution of fractions obtained by sieving and sanding.

TABLE 1

| Process: | Sample: | Yields: |
|---|---|---|
| — | Dried cloudberry press cake | 100% |
| Separation of seeds from press cake by sieving | Sieved seeds | 93% |
|  | Skin fraction | 7% |
| Sanding of sieved seeds (sanding time 15 min) | Sanded seeds | 69% |
|  | Seed coat powder | 11% |
|  | Loss | 13% |

Example 2: Sanding of Cloudberry Seeds Separated from Press Cake

A dried pressed cake of cloudberry from a commercial juice pressing process was sieved. The seeds were separated from the skin fraction by using a vibratory sieve shaker with a 1.60 mm screen at settings of 5 minutes sieving time and 1.5 mm amplitude. The seeds were sanded by using an abrasive machine (barley pearling machine) for 15 minutes sanding time. The yields of the sieving and sanding fractions and distribution of fractions obtained by sieving and sanding are shown in Table 2.

TABLE 2

| Process: | Sample: | Yields: |
|---|---|---|
| — | Dried cloudberry press cake | 100% |
| Separation of seeds from press cake by sieving | Sieved seeds | 96% |
|  | Skin fraction/Dry fraction A | 4% |
| Sanding of sieved seeds (sanding time 15 min) | Sanded seeds | 74% |
|  | Seed coat powder/Dry fraction B | 18% |
|  | Loss | 4% |

Example 3: Sanding of Raspberry Seeds Separated from Press Cake

Frozen raspberries were thawed and crushed with a pestle. The crushed raspberries were warmed up to 45° C. and iopectinase Super 8× enzyme was added. The enzyme dosage was 100 nkat/g berries (i.e. 1.98 ml/1 kg berries, active 51000 nkat/ml). After the incubation time (4 hours), juice pressing was performed by a High Pressure Tincture Press H P5 presser. The amount of press cake was 16% by weight and the dry matter of the press cake was 48% by weight. The press cake was dried by a quick drying machine with an air flow at 45° C. to a dry matter of 89%.

Seeds were separated from the dried press cake by using a vibratory sieve shaker with a 0.63 mm screen at settings of 5 minutes sieving time and 1.0 mm amplitude. The seeds were sanded by using an abrasive machine (barley pearling machine) for 15 minutes sanding time. The yields obtained by the different process steps and distribution of fractions obtained by the sieving and the sanding machines are shown in Table 3.

TABLE 3

| Process: | Sample: | Yields: |
|---|---|---|
| — | Dried raspberry press cake | 100% |
| Separation of seeds from raspberry press cake by sieving | Sieved seeds | 96% |
|  | Skin fraction/Dry fraction A | 4% |
| Sanding trial I: |  |  |
| Sanding of sieved seeds (sanding time 1 min) | Sanded seeds | 73% |
|  | Seed coat powder/Dry fraction B | 4% |
|  | Loss | 19% |
| Sanding trial II: |  |  |
| Sanding of sieved seeds (sanding time 2 min) | Sanded seeds | 72% |
|  | Seed coat powder/Dry fraction B | 7% |
|  | Loss | 17% |

Example 4: Sanding of Seeds Separated from Cloudberries

Cloudberries were frozen and freeze-dried. The dried cloudberries (less than 15 wt % of water) were crushed by hand to separate the skin, fruit flesh and seed portion from the whole berries. The seeds were separated from the skin and fruit flesh portion by using a vibratory sieve shaker with a 1.6 mm screen. The cloudberry material was first sieved using the 5 minutes sieving time and 1.0 mm amplitude and after that sieved by using the same sieve settings with ten glass balls. The glass balls assisted to separate the fruits flesh and skin from the seeds. After that the seeds were sanded using an abrasive machine (barley pearling machine) for 15 and 30 minutes sanding time. The yields obtained by the different process steps and distribution of fractions obtained by sieving and sanding are shown in Table 4.

TABLE 4

| Process: | Sample: | Yields: |
|---|---|---|
| — | Freeze-dried cloudberries | 100% |
| Seeds separating from berries by sieving twice (without and with 10 glass balls) | Sieved seeds | 48% |
|  | Skin and fruit flesh fraction | 52% |
| Sanding trial I: |  |  |
| Sanding of sieved seeds (sanding time 15 min) | Sanded seeds | 38% |
|  | Seed coat powder/Dry fraction B | 4% |
|  | Loss | 6% |
| Sanding trial II: |  |  |
| Sanding of sieved seeds (sanding time 30 min) | Sanded seeds | 39% |
|  | Seed coat powder/Dry fraction B | 6% |
|  | Loss | 3% |

Example 5: Fermentation of Cloud Berries, Pressing and Sieving

Fermentation

Frozen, ripe cloudberries (*Rubus chamaemorus*) were used as the berry material. The berry material was first heat treated and then inoculated with approximately $10^6$ cfu $g^{-1}$ of washed LAB cells. *Pedicoccus pentosaceus* VTT E-072742 from VTT Culture Collection was used as a starter culture in the fermentation of cloudberries (http://culturecollection.vtt.fi/). Prior to fermentations, the strain was refreshed in de Man Rogosa Sharpe broth for 1 day in a 100% carbon dioxide atmosphere which was created using anaerobic jars and Anaerocult C strips. The cells were collected from refreshed cultures by centrifugation and washed once in Ringer's solution. The fermentations were performed in a 6 kg scale in a 15-l capacity bioreactor for 3 days at 30° C. under constant mixing (130 rpm). The bioreactor was purged with sterile-filtered nitrogen gas in order to create anaerobic conditions. The viable counts of lactic acid bacteria and yeasts were determined before and after the fermentations using plate count technique. The results were expressed as colony-forming units (CFU) per gram of wet weight. The fermented berry mash was stored frozen.

Pressing and Drying

After fermentation the berry mash was treated with a hydraulically operated high-pressure tincture press using 5 litres filling material to separate juice and insoluble press cake.

The press cake from juice pressing was dried in a fluid bed dryer using +45° C. air flow, until the water content of the berry press cake was below 15% by weight. After that, the dried berry press cake was dry sieved using different sieve sizes or using a suction apparatus. A skin fraction having average particle less than 1250 μm was separated and seed fraction having average particle size of more than 750 μm was collected.

The mass yields of cloudberry press cake (fermented and non-fermented samples) were 8-10%. About 5% of the press cake consisted of peels and pulp, and remaining 95% were seeds.

Example 6: Testing of Antimicrobial Activity of Berry Material

Antimicrobial activity of berry material was tested against selected microbes including *Staphylococcus aureus, S. epidermidis, Pseudomonas aeruginosa, Salmonella typhimurium, Escherichia coli* and *Candida albicans*. Berry materials were extracted with acetone for the study.

Acetone extracts were prepared by dissolving 1 g of freeze-dried plant material to 50 ml of 70% acetone (v/v) which was made acidic by ascorbic acid (final concentration of ascorbic acid 0.1%) in order to stabilize phenolic compounds. Extraction was carried out using magnetic stirring (300 rpm, room temperature for 1 h). Suspensions were centrifuged (4000 rpm, 10 min, +4° C.), solid material was discarded and acetone was evaporated from the liquid phase with rotavapor at +35° C. water bath, 100 rpm, automatically adjusted vacuum. The remaining water phase was frozen and freeze-dried. Extraction can also be carried out without ascorbic acid using only 70% acetone (v/v).

Antimicrobial activities were measured in liquid cultures. Freeze-dried berry extracts of 1 mg $ml^{-1}$ were suspended into microbial cultures. Microbial culture without berry material was used as positive control, and culture with antibiotic (chloramphenicol for bacteria or hygromycin B for *C. albicans*) was used for negative growth control. The microbial cultures were incubated in their optimal growth conditions, and growth by cell counts was followed by plate count during 24 h of cultivation.

Figure 4:
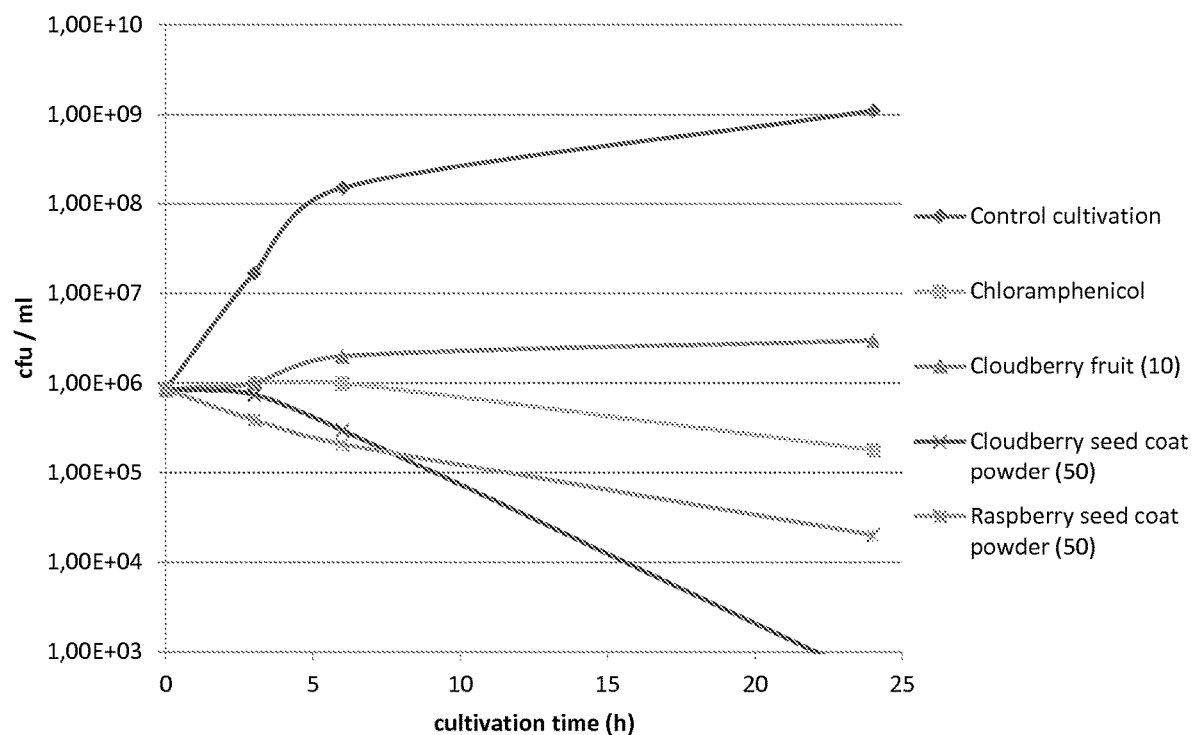
FIG. 4 shows antimicrobial activity of berry material.

The results show clear bactericidal activity of acetone extracts of cloudberry and raspberry fractions against *Staphylococcus aureus*) and *S. epidermidis* compared to positive control culture with no antimicrobial agents. Moderate growth inhibition was detected with *Pseudomonas aeruginosa*, *Escherichia coli* and *Salmonella typhimurium*. *Candida albicans* was not inhibited by these cloudberry and raspberry extracts. FIG. 4 shows the antimicrobial activity of acetone extracts (1 mg ml$^{-1}$) of cloudberry and raspberry fractions against *Staphylococcus aureus* in liquid culture during cultivation for 24 hours. Culture with antibiotic chloramphenicol was used as negative control. The tested samples were control samples, cloudberry fruit, cloudberry seed coat fraction and raspberry seed coat fraction.

Example 7: Antimicrobial Activity of Cloudberry Seed Coat Fractions

Antimicrobial activity of cloudberry seed coat fractions against *Staphylococcus aureus*, an important skin pathogen, in nanocellulose cleaning wipes, was tested in this example.

Water extracts were prepared of cloudberry coat powder by dissolving 1 g of freeze-dried material to 50 ml of water or acidic water (0.1% ascorbic acid is added to stabilize phenolic compounds). Extraction was carried out in microwave oven, heating two times 30 seconds and by mixing the suspensions well before, between and at the end of heating. Suspensions were centrifuged (4000 rpm, 10 min, +4° C.), solid material was discarded and supernatants were frozen and freeze-dried.

In addition, two types of acetone extracts were prepared: basic acetone extract of cloudberry coat powder (see Example 6), and more purified acetone extract of cloudberry fruit. The purification was made from basic acetone extraction as follows: For further purification of the extracts from sugars and organic acids solid-phase extraction with Sep-Pak C18 columns was used. Phenolic compounds were eluted from the column with ethanol or methanol or acidic ethanol or acidic methanol (acidic conditions were used to stabilize phenolic compounds). Solvent was evaporated and the compounds were diluted with water, frozen and freeze-dried, resulting in a rich powder with phenolic compounds.

The extracts were dissolved in sterile water in following concentrations: pure acetone extracts of cloudberry (1 mg ml$^{-1}$), basic acetone extract of cloudberry coat powder (2.5 mg ml$^{-1}$), and water extract of cloudberry coat powder (4.5 mg ml$^{-1}$). Two ml of each solution were placed on the wipe sheets, followed by 200 µl of bacterial suspension (1.2×10$^5$ cells). Two ml of sterile water with no berry extract was used for positive control of bacteria growth. Six parallel sheets were prepared of each sample and control. Immediately after inoculation of bacteria, three sheets of each sample and control were mixed with 20 ml of peptone saline in Stomacher, and the bacterial counts were measured by plate count method from the sheet suspensions. Their parallel sheets were treated similarly after incubation at 37° C. for 24 h.

Figure 5:
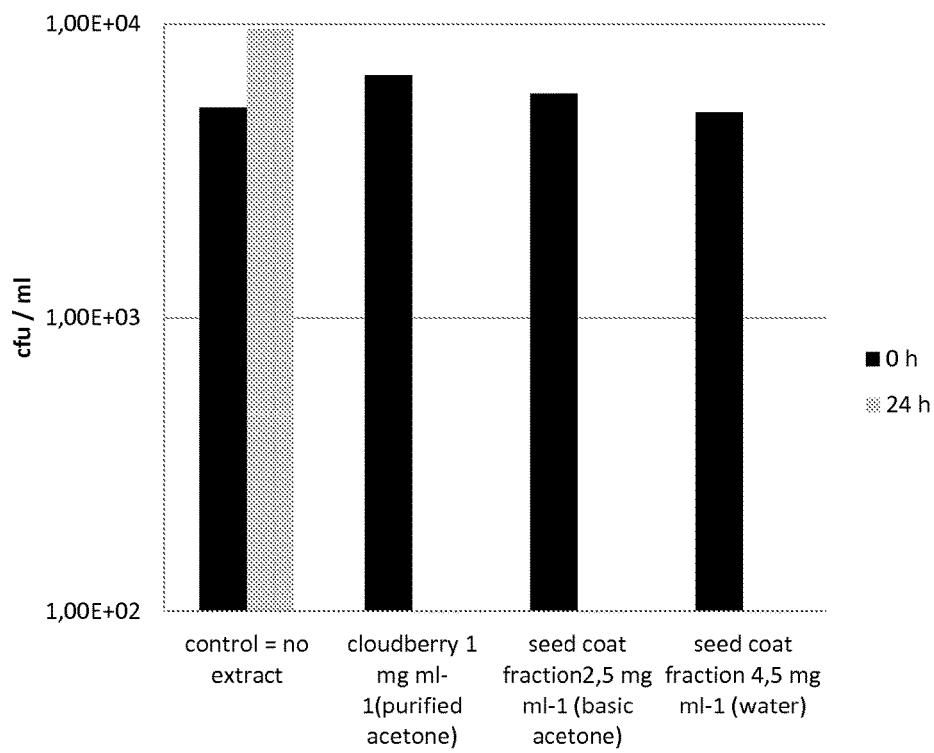
FIG. 5 illustrates antimicrobial activity of cloudberry extracts in wipes.

The results show that nanocellulose wipes supplemented with cloudberry fruit extract and cloudberry seed coat powder extracts have strong antimicrobial activity against *Staphylococcus aureus* after 24 hour incubation. The detection limit for bacterial plate counts was 100 cells ml$^{-1}$, and in all the wipes with berry extract the bacterial count decreased under this limit after 24 h of incubation. FIG. 5 shows antimicrobial activity of cloudberry extracts in nanocellulose wipes against *Staphylococcus aureus*. Bacterial counts in wipes were measured at 0 h (■) and after incubation of 24 h (▒) at 37° C. The detection limit for bacterial count was 100 cfu ml$^{-1}$.

Example 8: Enzyme Treatment of Sanded Seeds

Sanded cloudberry seeds were first soaked in water overnight. Then the seeds were treated with enzyme mixture of cellulose, pectinase and xylanase (Econase CE, dosage 30 FPU/g seeds; Pectinex Ultra, dosage 3000 nkat/g and Depol 740, dosage 3000 nkat/g) at 40° C. in ammonium acetate buffer, pH 4 for 22 h. After the enzyme treatment the seeds were dried in oven. The reference seeds were incubated in the buffer without the enzymes. The fatty acids were analysed from the dried seeds after the treatments. Yields of the fatty acids were 5.1 mg/g and 7.1 mg/g from the reference and enzyme treated seeds, respectively. The results show that fatty acids are more easily liberated from the sanded seeds that have been treated with enzymes compared to only sanded seeds.

Figure 6:
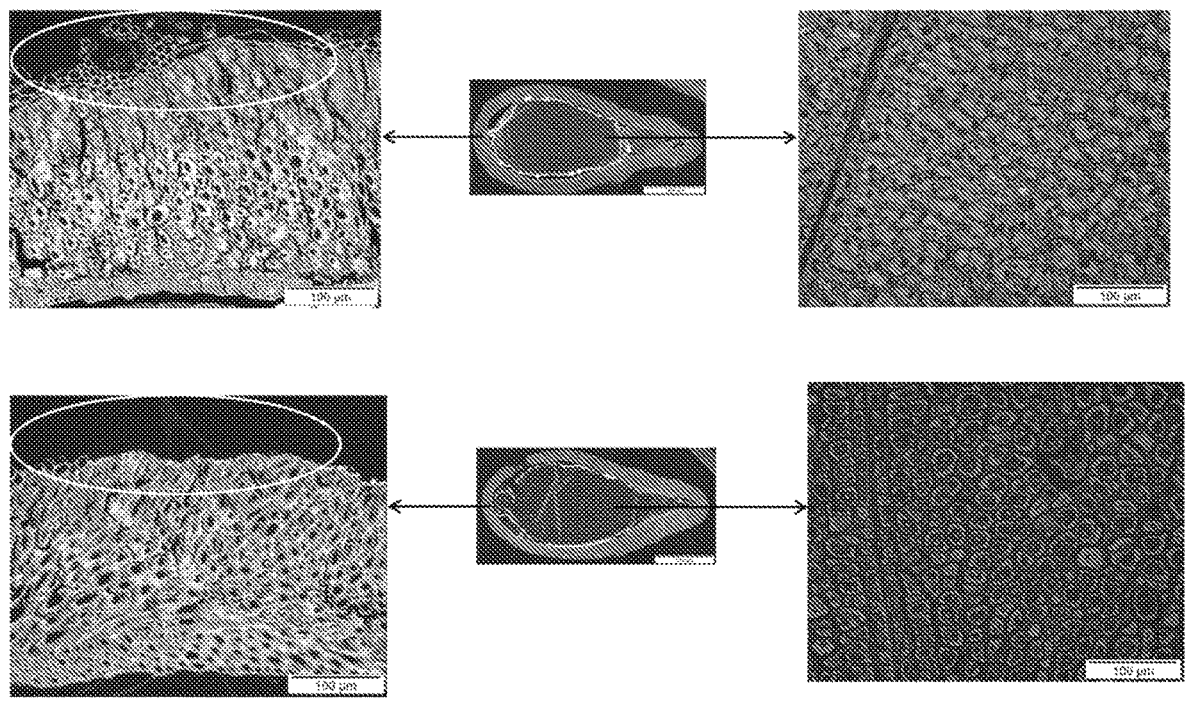
FIG. 6 presents microscopy photos of the surface of cloudberry seeds.

The outer surface and inside structure of the cloudberry seed is changed due to sanding and enzyme treatment. This can been in FIG. 6, presenting microscopy photos of the surface cross-section of the cloudberry seed. The upper figure shows cloudberry reference seed that has not been sanded, and the lower figure shows the sanded and enzyme treated seed. Lignin layer is thinner in treated seeds and it contains some holes compared to reference seed. The protein and beta-glucan structures are also different in treated seeds compared to reference showing that the enzyme treatment has affected also the inner part of the seed. The sanded and enzyme-treated cloudberry seeds are particularly suitable as a healthy ingredient in foods, food supplements, nutraceuticals, and in animal feeds, such as muesli.

Example 9: Antimicrobial Activity of Cloudberry Seed Coat Fractions Against *Staphylococcus aureus* and *S. epidermis* in Oily and Basic Creams, in Cosmetic Masks and in Toners Antimicrobial activity of cloudberry seed coat fractions against *Staphylococcus aureus* and *S. epidermis*, important skin pathogens, are tested in this example in oily and basic creams, in cosmetic masks and in toners.

Sanded seed powder is used as such, and water or ethanol extracts, acetone extracts and purified acetone extracts are prepared as described in Examples 6 and 7.

The extracts are dissolved in sterile water in following concentrations: pure acetone extracts of cloudberry (1 mg ml$^{-1}$), basic acetone extract of cloudberry coat powder (2.5 mg ml$^{-1}$), and water or ethanol extract of cloudberry coat powder or sanded seed powder as such (4.5 mg ml$^{-1}$). Extracts are added to the tested products to reach the following final concentrations: pure acetone extracts of cloudberry (0.01-2.0 mg/ml), basic acetone extract of cloudberry coat powder (0.1-2.0 mg/ml) and water or ethanol extract of cloudberry coat powder or sanded seed powder as such (0.1-5.0 mg/ml). Alternatively the extract powders are directly added to the tested products to the same final concentration. Each mixture was infected by bacterial suspension (1-2×10$^5$ cells). Sterile water with no berry extract is used for positive control of bacteria growth. Six parallel samples and control are prepared. Immediately after inoculation of bacteria, three samples and control are mixed with peptone saline, and the bacterial counts are measured by plate count method from the suspensions. Their parallel samples are treated similarly after incubation at 37° C. for 24 h.

The results show that oily creams, basic creams, cosmetic masks and toners supplemented with cloudberry seed coat powder extracts or the powder as such have moderate to strong antimicrobial activity against *Staphylococcus aureus* and *S. epidermis* after 24 hour incubation. The detection limit for bacterial plate counts is 100 cells ml$^{-1}$, and in all products with berry extract the bacterial count decrease under this limit after 24 h of incubation.

Example 10: Antimicrobial Activity of Cloudberry Seed Coat Fraction Against *Staphylococcus aureus* and *S. epidermis* in Cosmetic Exfoliator Cream Antimicrobial activity of cloudberry seed coat fraction against *Staphylococcus aureus* and *S. epidermis*, important skin pathogens, is tested in this example in cosmetic exfoliator cream.

Sanded cloudberry seed powder as such is added to exfoliator cream. The sanded cloudberry seed powder contains insoluble carbohydrate and fibre particles which act as natural (not synthetic) exfoliating particles. Sanded seed powder is mixed to the basic exfoliator cream to final concentration (0.1-5.0 mg/ml). In addition, seed powder extracts as prepared in Examples 6-8 can be added to give the product additional antimicrobial effects. Final concentrations of the extracts described in Examples 6-8 are used.

Results with voluntary subjects who use the exfoliator cream (for one week) with berry ingredients show clear softening and clarification of the skin after few days of use compared to control exfoliator cream (no added berry ingredients). Antimicrobial effects are shown as in example 9.

While the invention has been described with respect to specific examples including presently preferred modes of carrying out the invention, those skilled in the art will appreciate that there are numerous variations and permutations of the above described embodiments that fall within the spirit and scope of the invention. It should be understood that the invention is not limited in its application to the details of construction and arrangements of the components set forth herein. Variations and modifications of the foregoing are within the scope of the present invention.

The invention claimed is:

1. A process for converting berry and/or fruit materials to fractions comprising bioactive compounds with antimicrobial activity, wherein the process comprises the steps,
   sieving at least one berry material or fruit material selected from berries, fruits, by-products, side streams and waste materials originating from berries or fruits, and any combinations thereof, having water content not more than 15 wt %, whereby a seed fraction is separated from a skin fraction,
   sanding the seed fraction, whereby a seed coat fraction comprising 2-40 wt % of said surface layer of the seeds and a sanded seed fraction comprising the sanded seeds are obtained, and
   extracting bioactive compounds with antimicrobial activity from the seed coat fraction comprising the 2-40 wt % of said surface layer, wherein the berries are selected from the group consisting of the genus *Rubus*, *Sorbus*, *Rosa*, *Empetrum*, *Aronia* and *Hippophae* and combinations thereof, and the fruit are selected from the group consisting of the genus *Vitis*, *Punica*, *Pyrus* and *Malus*, and combinations thereof.

2. The process according to claim 1, wherein the process further comprises, prior to sieving, subjecting the berry material or fruit material to heat treatment, fermentation, enzymatic treatment, pressing, squeezing or drying, and combinations thereof.

3. The process according to claim 2, wherein the enzymatic treatment comprises carbohydrate hydrolyzing enzymes.

4. The process according to any one of claims 1, 2 or 3, wherein the sieving is carried out using a sieving device, air classification device, air jet sieve device, screening device, rotary screen or screening device.

5. The process according to claim 1, wherein the berry material or fruit material has water content of 0.1-10 wt %.

6. The process according to claim 1, wherein the sanded seed fraction is treated with an enzyme selected from the group consisting of cellulase, pectinase, xylanase and combinations thereof to obtain enzyme treated sanded seed fraction.

7. The process according to claim 6, wherein the enzyme treated sanded seed fraction is subjected to extraction using a super critical extraction method and/or a solvent extraction method.

8. The process according to claim 1, wherein the sanded seed fraction is milled.

9. The process according to claim 1, wherein the fruit are selected from the group consisting of the genus *Punica*, *Pyrus* and *Malus*, and combinations thereof.

10. The process according to claim 1, wherein the seed coat fraction comprising 2-40 wt-% of said seed surface layer is obtained as a powder.

11. The process according to claim 1, wherein the berries are selected from the group consisting of the genus *Rubus* and *Rosa*, and combinations thereof.

12. The process according to claim 1, wherein the berries are selected from the group consisting of the genus *Rubus*, and combinations thereof.

13. The process according to claim 1, wherein the berries are cloudberries (*Rubus chamaemorus*).

14. The processing according to claim 1, wherein the fruit are selected from the group consisting of the genus *Punica*.

* * * * *